United States Patent [19]

Itoh

[11] Patent Number: 5,754,617
[45] Date of Patent: May 19, 1998

[54] X-RAY CT INSPECTION EQUIPMENT FOR CONTAINER AND METHOD OF INSPECTING CONTAINER USING X-RAY CT INSPECTION

[75] Inventor: Sin-ichi Itoh, Kawasaki, Japan

[73] Assignee: Hitachi, Ltd., Tokyo, Japan

[21] Appl. No.: 618,609

[22] Filed: Mar. 20, 1996

[30] Foreign Application Priority Data

Mar. 28, 1995 [JP] Japan .................................. 7-069129

[51] Int. Cl.⁶ .................................................. H05G 1/60
[52] U.S. Cl. .................................................. 378/4; 378/57
[58] Field of Search .................................. 378/4, 20, 57

[56] References Cited

U.S. PATENT DOCUMENTS 5,367,552  11/1994  Perchmann .................................. 378/4

Primary Examiner—Craig E. Church
Attorney, Agent, or Firm—Antonelli, Terry, Stout, & Kraus, LLP

[57] ABSTRACT

X-ray CT inspection equipment for inspecting the contents of a container includes an inspection building having a container inlet port for receiving a container, serving as an item to be inspected at an inspection position inside of the building, and a container outlet port for allowing the container to exit the building after an inspection; a X-ray CT inspection apparatus provided at the inspection position in the inspection building; and a rail member for transporting the container to said inspection position where the X-ray inspection apparatus is located by transporting and the container from the container inlet port into the inspection building and, after the container has been inspected, transporting the container to the outside of the building through the container outlet port. Therefore, through only X-ray CT inspection of the container itself, a condition (relative density, structure) or freight accommodated in the container can be accurately imaged and displayed.

18 Claims, 3 Drawing Sheets

X-RAY CT INSPECTION EQUIPMENT FOR CONTAINER AND METHOD OF INSPECTING CONTAINER USING X-RAY CT INSPECTION

BACKGROUND OF THE INVENTION

The present invention relates to X-ray CT (computerized tomography) inspection equipment for inspecting the contents of a container and a method of inspecting the contents b a container using X-ray CT inspection; and, more particularly, the invention relates to X-ray CT inspection equipment and a method using X-ray CT inspection suitable for observing freight in a container which is to be inspected using X-ray CT inspection employing a X-ray under a condition where the freight is inspected while it is in the closed container.

In recent years, a freight which involves imported goods carried in a container, there are many cases in which guns, narcotics and hemps are sealed together. Therefore, it is important to perform an inspection of the freight at the airport or harbor where the goods arrive. However, in the case of narcotics, since the narcotics are often mixed with other filler material, it becomes difficult to discriminate the narcotics from the filler material.

Up to now, many inspection methods have been proposed for detecting the above stated materials, such as an inspection method which relies on personal inspection by a human, an inspection method using a metal detector, and an inspection method using X-ray permeation tomography.

Recently, use has been made of equipment for inspecting questionable material employing an inspection method using X-ray permeation tomography, where a high energy (6–8 MeV) X-ray is employed. With this inspection equipment, a container is inspected by computerized-tomography without opening it, so that the questionable material carried in an interior portion of the container cam be detected.

However, this X-ray permeation tomography inspection method has the following problems concerning the adaption range of this inspection method.

(1) The permeative force of the high energy X-ray must be excessively large when the container is constructed of or contains a low density material, and so, in many cases, it is difficult to comprehend the exact forms (figures, shapes) of the contained materials from the obtained image. Therefore, this method mainly is limited to determination of the existence of metal materials in the container (for example, guns etc.).

(2) In a case where low density materials are contained in a container made of a thick metal material, since the X-ray is affected by the metal material, it is difficult to detect the existence of a low density material.

(3) It is difficult to discriminate freight which is constituted by various kinds of high density materials and low density materials.

As a result, this inspection method, in which the container is inspected by X-ray permeation inspection without opening the container, is effective from the point of view of the efficiency of the inspection, however it is impossible to obtain full information sufficient for making a reasonable judgment about the contents of freight including low density materials.

Recently, because of an increase in the malicious sending of dangerous materials, the necessity for accurately discriminating in detail the content of freight has suddenly increased, so that the need to employ an adaption of X-ray dislocation tomography (X-ray computerized tomography), in which the effectiveness of the above stated items (1), (2) and (3) is ensured, has become important.

However, at the present time, there is no X-ray CT inspection equipment which has been designed for exclusive use in the inspection of a container. Accordingly, without removing the freight from the container, the necessity for effective X-ray CT inspection equipment, in which the material density of the forms (figures, shapes) of the interior portion of the freight can be accurately determined, has become an important objective.

As conventional techniques, a method and an apparatus for inspecting the content of freight is disclosed in Japanese patent laid-open publication No. 92,940/1983, for example, and also a X-ray inspection apparatus for large scale freight is disclosed in Japanese patent laid-open publication No. 63,843/1987, for example.

SUMMARY OF THE INVENTION

The present invention has been developed with the above stated problems in mind, and an object of the present invention is to provide X-ray CT inspection equipment for inspecting the content of a container and a method of inspecting the content of a container using X-ray CT inspection, wherein by inspecting a container solely through X-ray CT inspection, a condition (relative density, structure) of freight accommodated in a container is accurately imaged and displayed.

So as to attain the above stated object of the present invention, according to the present invention, the following features are provided:

(1) X-ray CT inspection equipment for a container which includes an inspection building having an inlet port for receiving a container serving as an item to be inspected at an interior portion of the building and an outlet port for allowing the container to exit the building after inspection; a X-ray CT inspection apparatus provided in the inspection building; and a rail member for transporting the container from the inlet port to an inspection position where the X-ray CT inspection apparatus the inspection building and, after the container has been inspected, leads the container to the outside of the building through the outlet port.

(2) A X-ray CT inspection apparatus which includes a X-ray source, a detector and an annular-shaped rotative table for mounting the X-ray source and the detector with an opposing relationship; so that, when the container is positioned at a hollow portion of the rotative table, a X-ray beam from the X-ray source is irradiated on the container and freight in an interior portion of the container is inspected by computerized-tomography.

(3) A X-ray CT inspection apparatus which includes a X-ray source for irradiating a X-ray beam, a detector for receiving the X-ray beam irradiated from the X-ray source, a translation movement arrangement for respectively translation-moving the detector and the X-ray source, and an annular shaped rotative table for supporting the translation movement arrangement with the X-ray source and the detector being disposed on opposite sides of the hollow portion of the rotative table; so that, when a container is positioned at the hollow portion of the rotative table, the X-ray beam from the X-ray source is irradiated on the container and the X-ray beam is received at the detector, the X-ray source means and the detector means being stepped through a plurality of inspection positions by the translation movement arrangement.

(4) A X-ray CT inspection apparatus which includes a X-ray source, a detector and two annular-shaped rotative tables each mounting an X-ray source and a detector with an opposing relationship, the two rotative tables being vertically arranged with respect to the floor of the inspection building and rotatively installed on a wall of a support stand of the inspection building; and, in order to symmetrically arrange the two hollow shaped rotative tables with a 180° disposition, the two annular-shaped rotative tables are mounted in a back to back relationship on opposite faces of a wall of a support stand which is provided on the floor of the inspection building.

(5) X-ray CT inspection equipment for inspecting a container, which includes an inspection building having inlet port for receiving a container serving as an item to be inspected at an interior portion of the building and an outlet port for allowing the container to exit the building after inspection; a X-ray CT inspection apparatus for inspecting the content of a container which has been carried into the inspection building; a movement stand for mounting the X-ray CT inspection apparatus; and a rail member for transporting the container from the inlet port to the outlet port past the X-ray CT inspection apparatus.

(6) A movement stand member which includes a movement unit and a vertical stand member having a hollow portion; and a X-ray CT inspection apparatus installed on a side face of the stand member having a rail member, the rail member being arranged to pass through the vertical stand member and a hollow portion of an annular-shaped rotating table.

(7) A method of inspecting a container using X-ray CT inspection which includes the steps of transporting a container on a trolley into an inspection building through a container inlet port to an inspection position in the vicinity of a X-ray CT inspection apparatus; stopping the trolley when a tip end of the container reaches the inspection position at the X-ray CT inspection apparatus; moving an accelerator and a detector of the X-ray CT inspection apparatus so that the accelerator of the X-ray CT inspection apparatus moves along a translation movement arrangement and the detector moves along a translation movement arrangement in parallel with each other; computerized-tomographing an interior portion of the container by irradiating a X-ray beam from the accelerator onto the container; and displaying a condition of an interior portion of the container in which freight is accommodated.

(8) A method of inspecting a container using X-ray CT inspection which includes the steps of rotating a rotatable table carrying an X-ray source and a detector of the X-ray CT inspection apparatus to a predetermined angle at a first position where the container stops; carrying out an inspection of the container using the X-ray CT inspection apparatus at said first position; and repeating the steps of rotating the table and carrying out inspection of the container until the X-ray source and detection of the X-ray CT inspection apparatus through 180° by rotating the table through incremental steps of a predetermined angle.

(9) A method of inspecting a container using X-ray CT inspection which includes the steps of transporting a container prior to inspection from a storage yard, using a trolley, through an inlet port of an inspection building; positioning a tip end of a transported container at a first inspection position where a first X-ray beam is irradiated on the container from a first accelerator carried by a first annular-shaped rotating table and so that a central area of the container is positioned at a second inspection position where a second X-ray beam is irradiated on the container from a second accelerator carried by a second annular-shaped rotating table; and carrying out an inspection of the container using the first X-ray beam from the tip end of the container to substantially said central area of the container, while carrying out an inspection of the container using the second X-ray beam from substantially the central area of the container to the end of the container opposite said tip end.

With the above stated features, the container can be inspected without opening it using CT inspection, and further, the condition (relative density, structure) of the freight accommodated in the container can be accurately judged.

DESCRIPTION OF THE INVENTION

Figure 1:
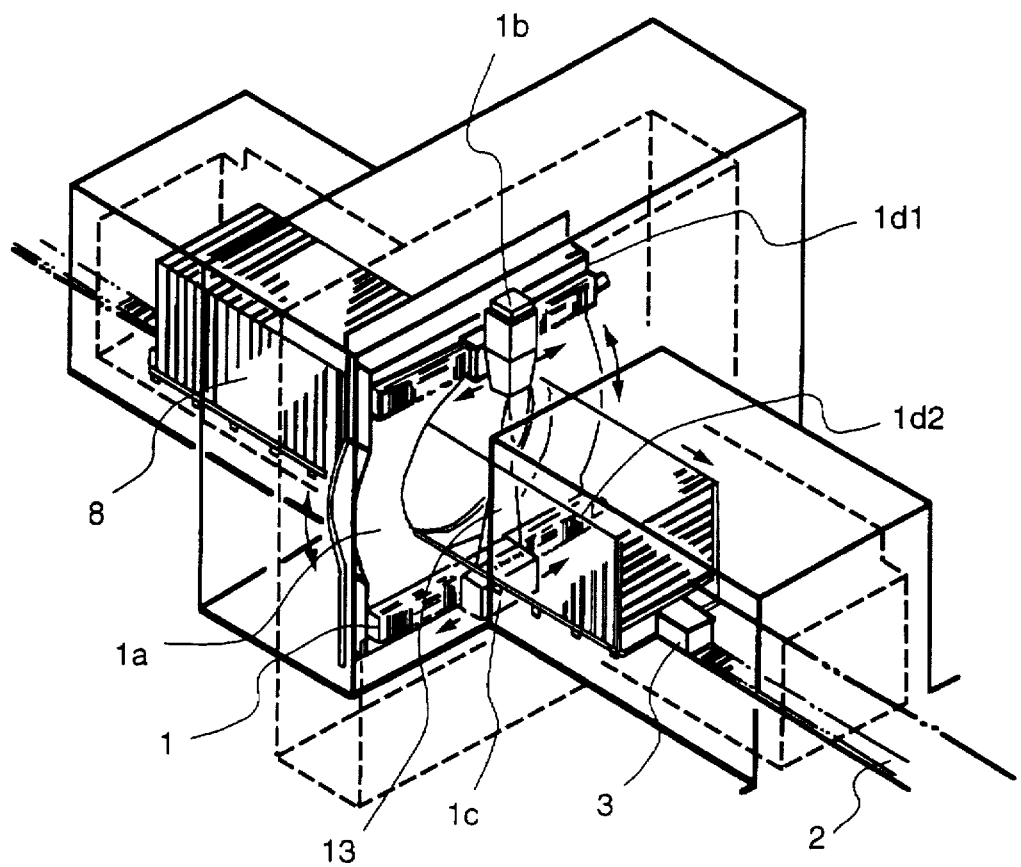
FIG. 1 is a schematic perspective view of X-ray CT inspection equipment for a container according to the present invention.

Hereinafter, one embodiment of X-ray CT inspection equipment for inspecting the contents of a container and a method of inspecting the contents of a container using X-ray CT inspection according to the present invention will be explained with reference to the drawing.

Figure 2:
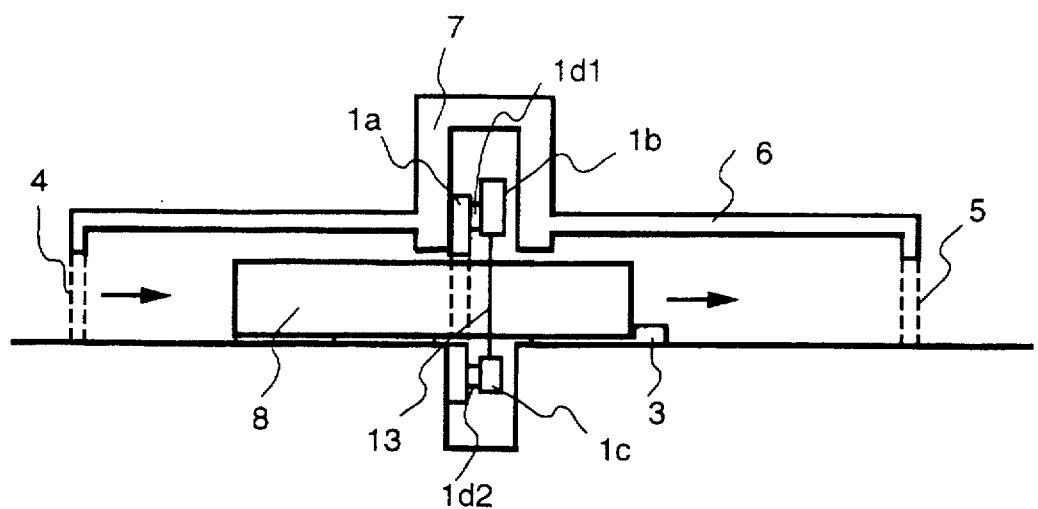
FIG. 2 is a longitudinal cross-sectional view of the X-ray CT inspection equipment for a container as shown in FIG. 1 according to the present invention.

FIG. 1 and FIG. 2 are directed to an embodiment of X-ray CT inspection equipment for inspecting the content of a container and which employs a method of inspecting the content of a container using X-ray CT inspection according to the present invention.

The X-ray CT inspection equipment roughly comprises X-ray CT inspection apparatus 1, a container transportation rail 2, a transportation trolley 3, an inspection building 6, and a support stand wall.

The support stand wall 7 made of concrete is arranged at a central portion of the inspection building 6 and projects from every side of the inspection building 6. The X-ray CT inspection apparatus 1 is disposed at a side face of an inner portion of the support stand wall 7, as seen in FIG. 2.

The container transportation rail 2 is mounted so as to transport a container 8 as an item to be inspected into the inspection building 6 and to guide the container 8 to an inspection position where the X-ray CT inspection apparatus 1 is located.

After the inspection of the container 8 is completed, the container transportation rail 2 leads the container 8 to the outside of the inspection building 6. The transportation trolley 3 transports the container 8 on the transportation rail 2.

A container inlet port 4 and a container outlet port 5 are provided on the inspection building 6. A pit is formed by digging a hole to a predetermined depth from the ground level at a bottom portion of the support stand wall 7. The support stand wall 7 projects outwardly from every side at substantially the central portion of the inspection building 6. In other words, a lower portion of the container transportation rail 2 is disposed at substantially the center of the inspection building 6. Therefore, the X-ray CT inspection apparatus 1 can rotate around the container 8 as the item is being inspected.

In FIG. 2, the outline of the above stated X-ray CT inspection apparatus 1 is shown. As shown in FIG. 2, the X-ray CT inspection apparatus 1 comprises a annular-shaped rotating table 1a, an accelerator (X-ray source) 1b, a detector 1c and two translation movement units 1d1 and 1d2.

The annular-shaped rotating table 1a is rotatively installed along the side face of the interior portion of the support stand wall 7. The container transportation rail 2 is positioned so as to pass through a lower portion of the hollow interior of the annular-shaped rotating table 1a.

The accelerator 1b is fixed to the translation movement unit 1d1 and the detector 1c is fixed to the translation movement unit 1d2. These translation movement units 1d1 and 1d2 are arranged in parallel on opposite sides of the hollow portion of the rotating table 1a.

A X-ray beam 13 from the accelerator 1b is irradiated onto the container 8, which is positioned within the hollow portion of the rotating table 1a. The irradiated X-ray beam 13 is received by the detector 1c as the accelerator 1b is moved along the translation movement unit 1d1 and the detector means 1c is moved along the translation movement unit 1d2.

Further, the container transportation rail 2 is disposed along a path from the container inlet port 4 of the inspection building construction 6 to the container outlet port 5 through the hollow portion of the rotating table 1a. The container 8 mounted on the transportation trolley 3 is moved on the container transportation rail 2 in accordance with the progress of CT tomography.

Figure 3:
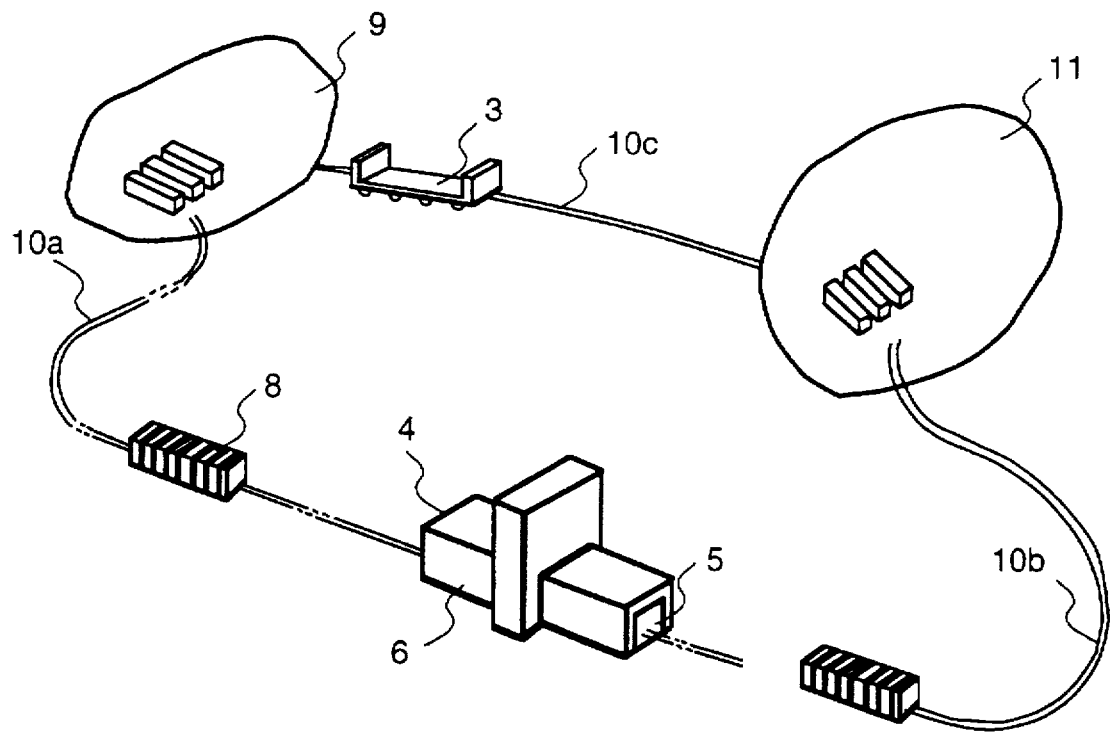
FIG. 3 is a diagrammatic view showing an arrangement of the X-ray CT inspection equipment in a storage yard according to the present invention.

FIG. 3 shows an arrangement between the X-ray CT inspection equipment and a storage yard 8 for effectively carrying out the X-ray CT inspection according to the present invention. As shown in FIG. 3, the container 8, prior to inspection, is stored in a yard 8. A transportation rail 10a extends to the container port 4 of the inspection building 6 and a transportation rail 10b is disposed so as to transport the container 8 from the outlet port 5, after the inspection, to a storage yard 11.

Further, after the inspected container 8 is transported to the storage yard 11, a transportation rail 10c is disposed so as to return the trolley 3 having no load, from the storage yard 11 to the storage yard 9. The transportation rails 10a and 10b are continuously connected to a transportation rail (not shown) which is in the interior portion of the inspection building 6.

Next, a method of inspecting the container 8 using the X-ray CT inspection equipment according to the present invention will be explained with reference to FIG. 1 to FIG. 3.

First of all, the containers 8 to be inspected, which are accumulated in the storage yard 9, are mounted on a trolley 3, and the trolley 3 is transported along the transportation rail 10a through the container inlet port 4 and is conveyed into the inspection building 6. The trolley 3 is transported in the vicinity of the X-ray CT inspection apparatus 1, and when a tip end of the container 8 reaches the inspection position of the X-ray CT inspection apparatus 1, the trolley 3 is stopped.

When the trolley 3 stops, a predetermined check is made before the inspection is carried out; and, after that, the container 8 is moved through a predetermined distance along the rail, and then the container 8 is stopped again. At this position of the container 8, the accelerator 1b of the X-ray CT inspection apparatus 1 is moved along the translation movement unit 1d2 and also the detector 1c is moved along to the translation movement unit 1d2. The accelerator 1b and the detector 1c parallel, and the X-ray beam 13 is irradiated from the accelerator 1b so that the interior portion of the container 8 is computerized-tomographed. The computerized-tomographed image of the interior portion of the container 8 is detected by the detector 1c and is picture-imaged in a SRT (not shown); therefore, the condition (relative density, structure) of an interior portion of the freight is accurately displayed.

Next, while maintaining the container 8 in this position, the rotative table 1a of the X-ray CT inspection apparatus 1 is rotated by a predetermined angle (for example, 15°) and at the rotated position, an inspection using the X-ray CT inspection apparatus 1 is carried out similar to that described above. Therefore, the condition (relative density, structure) of the freight, which is accommodated in the container 8, is inspected at the predetermined rotated position. Next, the rotative table 1a of the X-ray CT inspection apparatus 1 is rotated once again by the above stated predetermined angle and inspection is performed, until this inspection procedure has been carried out repeatedly at spaced angles through 180° of rotation of the X-ray CT inspection apparatus 1. Accordingly, the above stated inspection is carried out at the first stopped position twelve times, for example. At this point, the inspection of the container 8 at the a first stopped position is finished.

Next, the container 8 is moved by a predetermined distance along the rail and the above stated inspection of the container 8 is carried out again. By carrying out this inspection at spaced positions along the whole length of the container 8, therefore, the condition (relative density, structure) of the freight in the container can be deleted.

The container 8, for which the inspection has been completed, is transported through the port 5 on the trolley 3 and is carried into the yard 11 on the transportation rail 10b. Herein, the inspected container 8 is unloaded from the trolley 3 and the container 8 is stored in the yard 11. Then, the trolley 3 is transported on the rail 10c into the storage yard 9 so that the trolley 3 may be reused again.

A modification of the X-ray CT inspection equipment according to the present invention will be explained with reference to FIG. 4.

Figure 4:
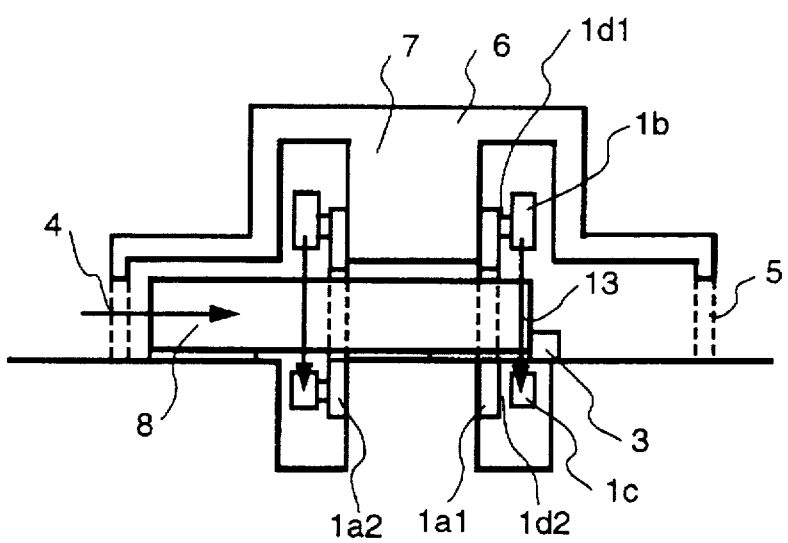
FIG. 4 is a longitudinal cross-sectional view of another X-ray CT inspection equipment for a container according to the present invention.

As seen in FIG. 4, two X-ray CT inspection apparatuses 1 are provided, therefore the inspection time is reduced by half and further the size of the inspection building 6 is also reduced. Namely, the support stand wall 7 made of concrete is projected toward the central portion of the inspection building 6 and extends into the interior portion thereof. The X-ray CT inspection apparatuses 1 are symmetrically arranged on opposing side faces of the concrete support stand wall 7.

In this case, two annular-shaped rotative tables 1a1 and 1a2 for supporting the X-ray CT inspection apparatuses 1 are symmetrically arranged both side faces of the concrete support stand wall 7 and are separated by a length of about ½ the length of the container 8.

The accelerator 1b, detector 1c and the two translation movement units 1d1 and 1d2 are respectively arranged on the two annular-shaped rotative tables 1a1 and 1a2; however, since each of these assemblies is comprised similarly to the single arrangement of FIG. 1, it will be unnecessary to explain the details thereof again.

Next, the method of inspecting the container 8 using the X-ray CT inspection equipment according to FIG. 4 will be explained.

The container 8 to be inspected is transported from the yard 9 into the inspection building 6 through the container inlet port 4 using a trolley 3 similar to the operation described above.

At first, the tip end of the transported container 8 is positioned at the inspection position of the X-ray beam 13 which is irradiated from the accelerator 1b of the rotative table 1a1. Accordingly, the irradiation position of the X-ray beam from the accelerator of the rotative table 1a2 is positioned at a central portion of the container 8, as seen in FIG. 4.

With the above stated condition, using the same method described with reference to FIGS. 1 and 2, the inspection of the container 8 is carried out. As can be seen, the inspection of the container 8 using the X-ray beam 13 from the accelerator 1b of the rotative table 1a1 will be finished just at the central portion of the container 8. Further, the inspection of the container 8 using the X-ray beam from the accelerator of the rotative table 1a2 is simultaneously carried out, and this inspection of the container 8 is carried out from the central portion to the end of the container.

With the above construction shown in FIG. 4, similar effects to those attained in the above stated first embodiment can be attained; and further, in comparison with the above stated first embodiment, the time for inspecting the whole length of the container 8 can be reduced by half. Also the space of the inspection building construction 6 can be made smaller in comparison with the above stated first embodiment.

A further modification of the X-ray CT inspection equipment for a container according to the present invention will be explained with reference to FIG. 5.

Figure 5:
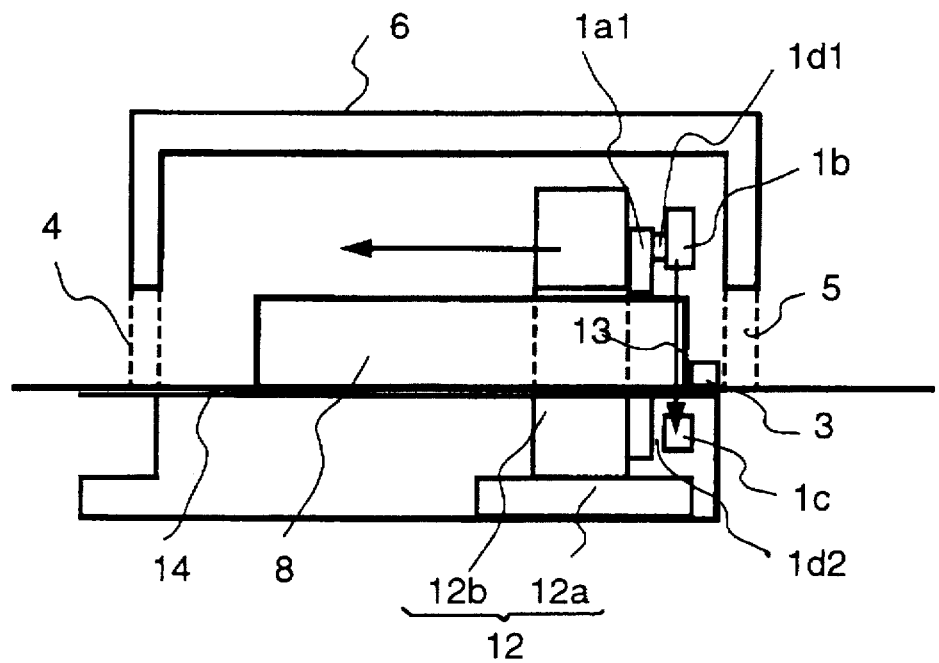
FIG. 5 is a longitudinal cross-sectional view of X-ray CT inspection equipment for a container according to the present invention.

The container X-ray CT inspection equipment according to FIG. 5 comprises X-ray CT inspection apparatus 1 similar to FIGS. 1 and 2, a movement stand 12 for mounting the X-ray CT inspection apparatus 1, and a stand 14 having a rail for mounting the container 8.

The movement stand 12 comprises a movement unit 12a and a vertical stand 12b having a hollow portion. The X-ray CT inspection apparatus 1 is installed in a side of the vertical stand 12b. The stand 14 carrying the rail 3 is arranged to pass through the vertical stand 12b and the hollow portion of the annular-shaped rotative table 1a1. The stand 14 carrying the rail is supported at both end portions of the main stand and provides a scanning space for the movement stand 12.

The method of inspecting a container using the X-ray CT inspection equipment according to FIG. 5 will be described. At first the container 8 is set at a predetermined position on the stand 14 carrying the rail and the X-ray beam 13 from the accelerator 1b is aligned with an end portion of the container 8. Therefore, the CT inspection can be carried out similar to the operation previously described.

According to the present invention, in accompaniment with the starting of the CT inspection, the movement stand 12 is moved toward the other end of the container 8, so that the inspection of the container 8 is carried out. With this inspection method, scanning distance becomes substantially equal to the length of the container 8, so that, in comparison with the first embodiment, the space for the inspection building construction 6 can be reduced by half.

Figure 6:
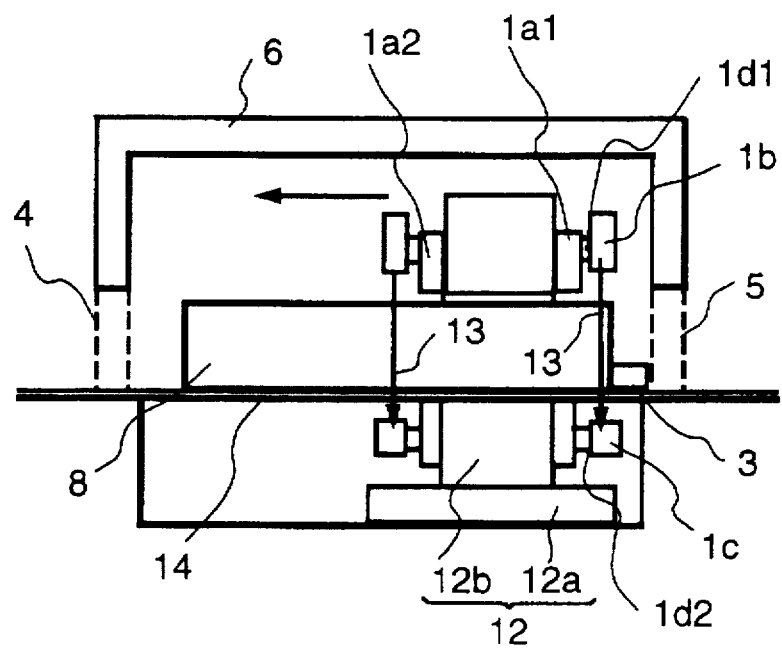
FIG. 6 is a longitudinal cross-sectional view of X-ray CT inspection equipment for a container according to the present invention.

A further modification of the X-ray CT inspection equipment for a container according to the present invention will be explained with reference to FIG. 6. The container X-ray CT inspection equipment according to FIG. 6 is similar to FIG. 5, but employs the equipment shown in FIG. 4. In this regard, two X-ray CT inspection apparatuses 1 are mounted on the movement stand 12.

In FIG. 6, two annular-shaped rotating tables 1a1 and 1a2 are fixed, respectively, on opposite side faces of the vertical stand 12b of the movement stand 12 and are spaced from each other by a length of about ½ of the length of the container 8.

The other elements mounted on the two annular-shaped rotating tables 1a1 and 1a2 are similar to the previously described arrangements. The stand 14 carrying the rail 3 is arranged to pass through the vertical stand 12b and the hollow portion of the rotating tables 1a1 and 1a2.

The method of inspecting the container 8 using the X-ray CT inspection equipment of FIG. 6 is substantially same as that described with reference to FIG. 4. However, in this case, the scanning distance becomes substantially half of the length of the container 8; therefore, the inspection time for the container 8 becomes half in comparison with that of the arrangement shown in FIG. 4.

As stated above, in the X-ray CT inspection equipment for a container which is exemplified in the drawings, as the container itself is the item to be inspected, the interior condition (relative density distribution, structure) of the container accommodating freight can be imaged, the contents of the freight can be accurately discriminated and further the inspection effects can be remarkably improved in comparison with the conventional case in which the individual containers are opened and inspected one by one.

In particularly, in the case of a refrigerated container, according to the inspection method of the present invention, the freight in the interior portion is not exposed to the air, so that the condition of the freight is not undesirably affected.

According to the X-ray CT inspection equipment and the inspection method for inspecting a container using X-ray CT inspection according to the present invention, numerous advantages can be obtained.

Since a container can be inspected without opening it using X-ray CT inspection, and further, since the condition (relative density, structure) of the freight accommodated in the container can be accurately judged, only by X-ray CT inspection of the container itself, the condition of the freight accommodated in the container can be accurately imaged and displayed.

What is claimed is:

1. A X-ray CT inspection equipment for inspecting the contents of a freight container, comprising:

an inspection building having a freight container inlet port for passing a freight container, serving as an item to be inspected, into an interior portion of said inspection building and a freight container outlet port for allowing the freight container to exit said inspection building after inspection;

a X-ray CT inspection apparatus provided in said inspection building, said X-ray CT inspection apparatus including a X-ray source, a detector and an annular-shaped rotatable table having a hollow portion at a center portion thereof, said annular-shaped rotatable table mounting said X-ray source and said detector; and a freight container transportation rail for transporting the freight container thereon from said inlet port of said inspection building to an inspection position of said X-ray CT inspection apparatus in said inspection building and, after the freight container has been inspected, for transporting the freight container to the outside of said inspection building through said freight container outlet port, so that when the freight container transported on said freight container transportation rail is positioned at said hollow portion of said annular-shaped rotatable table, contents of an interior portion of the freight container are computerized-tomography-inspected by rotating said annular-shaped rotatable table;

wherein said inspection building has a central portion which projects toward a lower portion accommodated in a pit formed by digging a hole to a predetermined depth from ground level, a lower portion of said freight container transportation rail being disposed at substantially a center of said inspection building, and said X-ray CT inspection apparatus is rotatable around said freight container along a path having a portion extending within the pit.

2. X-ray CT inspection equipment according to claim 1, further comprising:

a first freight container transportation rail which extends from said freight container inlet port of said inspection building to a first yard for storage of the freight container before inspection, and a second freight container transportation rail which extends from said freight container outlet port of said inspection building to a second yard for storage of the freight container after inspection.

3. X-ray CT inspection equipment according to claim 1, wherein:

said annular-shaped rotatable table mounts said X-ray source and said detector in an opposing relationship, so that when the freight container is positioned at said hollow portion of said annular-shaped rotatable table, a X-ray beam from said X-ray source is irradiated onto the freight container and the contents of the interior portion of the freight container are computerized-tomography-inspected.

4. X-ray CT inspection equipment according to claim 1, wherein:

said annular-shaped rotatable table mounts said X-ray source and said detector in an opposing relationship;

said annular-shaped rotatable table is vertically arranged with respect to a floor of said inspection building and is rotatively mounted on a wall of a support stand member of said inspection building; and said freight container transportation rail extends horizontally from said inlet port to said outlet port through said hollow portion of said annular-shaped rotatable table.

5. X-ray CT inspection equipment according to claim 1, wherein:

said annular-shaped rotatable table mounts said X-ray source and said detector in an opposing relationship; and said annular-shaped rotatable table is vertically arranged with respect to a floor of said inspection building and is rotatively mounted on a wall of a support stand member of said inspection building, a portion of said inspection building where said annular-shaped rotatable table is positioned projecting outwardly from every side of said inspection building.

6. X-ray CT inspection equipment according to claim 1, wherein:

said X-ray CT inspection apparatus further includes said X-ray source for irradiating a X-ray beam on the freight container, said detector for receiving said X-ray beam irradiated from said X-ray source on the freight container, first and second translation movement means for respectively translation-moving said detector means and said X-ray source alone linear paths, said annular-shaped rotatable table supporting said first translation movement means of said X-ray source and said second translating movement means of said detector on opposite sides of said hollow portion of said rotatable table with said X-ray source and said detector being disposed in an opposing relationship so that when the freight container is positioned at said hollow portion of said table, an X-ray beam from said X-ray source is irradiated onto the freight container and is received by said detector means.

7. X-ray CT inspection equipment according to claim 1, wherein:

said X-ray CT inspection apparatus further includes two annular-shaped rotatable tables each mounting an X-ray source and a detector in an opposing relationship;

said two annular-shaped rotatable tables being vertically arranged with respect to a floor of said inspection building and rotatively mounted on a wall of a support stand member of said inspection building so as to be rotatable through 180°;

said two annular-shaped rotatable tables being set in a back to back condition on a wall of said support stand member which is supported on said floor of said inspection building.

8. X-ray CT inspection equipment according to claim 1, wherein the freight container is a non-portable freight container, and a trolley carries the freight container along said freight container transportation rail.

9. A X-ray CT inspection equipment for inspecting the contents of a freight container, comprising:

an inspection building having a freight container inlet port for passing a freight container, serving as an item to be inspected, into an interior portion of said inspection building and a freight container outlet port for allowing the freight container to exit said inspection building after inspection;

a X-ray CT inspection apparatus provided in said inspection building, said X-ray CT inspection apparatus including a X-ray source, a detector and an annular-shaped rotatable table having a hollow portion at a center portion thereof, said annular-shaped rotatable table mounting said X-ray source and said detector; and a freight container transportation rail for transporting the freight container thereon from said inlet port of said inspection building to an inspection position of said X-ray CT inspection apparatus in said inspection building and, after the freight container has been inspected, for transporting the freight container to the outside of said inspection building through said freight container outlet port, so that when the freight container transported on said freight container transportation rail is positioned at said hollow portion of said annular-shaped rotatable table, contents of an interior portion of the freight container are computerized-tomography-inspected by rotating said annular-shaped rotatable table;

wherein said inspection building has a central portion which projects toward a lower portion accommodated in a pit formed by digging a hole to a predetermined depth from ground level, a lower portion of said freight container transportation rail being disposed at substantially a center of said inspection building, and said X-ray CT inspection apparatus is rotatable around said freight container along a path having a portion extending within the pit.

10. X-ray CT inspection equipment for inspection of the contents of a freight container comprising:

an inspection building having a freight container inlet port for passing a freight container, serving as an item to be inspected, into an interior portion of said inspection building and a freight container outlet port for allowing the freight container to exit said inspection building after inspection;

a X-ray CT inspection apparatus for inspecting the contents of the freight container at an inspection position in said inspection building;

a movement stand member for mounting said X-ray CT inspection apparatus in said inspection building; and a stand member having a freight container transportation rail in said inspection building for transporting the freight container to the inspection positions;

wherein said inspection building has a central portion which projects toward a lower portion accommodated in a pit formed by digging a hole to a predetermined depth from ground level, a lower portion of said freight container transportation rail being disposed at substantially a center of said inspection building, and said X-ray CT inspection apparatus is rotatable around said freight container along a path having a portion extending within the pit.

11. X-ray CT inspection equipment for inspection of the contents of a freight container comprising:

an inspection building having a freight container inlet port for passing a freight container, serving as an item to be inspected, into an interior portion of said inspection building and a freight container outlet port for allowing the freight container to exit said inspection building after inspection;

a X-ray CT inspection apparatus for inspecting the contents of the freight container at an inspection position in said inspection building;

a movement stand member for mounting said X-ray CT inspection apparatus in said inspection building;

a stand member having a freight container transportation rail in said inspection building for transporting the freight container to the inspection position;

said movement stand member comprises a movement unit and a vertical stand member having a hollow portion through which said freight container transportation rail extends for transporting a freight container;

said X-ray CT inspection apparatus is installed on a side face of said movement stand member by way of an annular-shaped rotatable table; and said movement unit of said movement stand member having means for moving said vertical stand member with said annular-shaped rotatable table along a section of said freight container transportation rail.

12. A method of inspecting the contents of a freight container using X-ray CT inspection, comprising the steps of:

transporting a freight container along a freight container transportation rail from a storage yard on a trolley through a freight container inlet port to an X-ray CT inspection apparatus in an inspection building having a central portion which projects toward a lower portion accommodated in a pit formed by digging a hole to a predetermined depth from ground level, a lower portion of the freight container transportation rail being disposed at substantially a center of the inspection building;

positioning a tip end of the transported freight container with respect to a stand member having the freight container transportation rail to a position of a first X-ray beam which is irradiated from a first X-ray source mounted on a first annular-shaped rotatable table on which another part of said X-ray CT inspection apparatus is supported;

positioning an irradiation position of a second X-ray beam from a second X-ray source mounted on a second annular-shaped rotatable table on which another part of said X-ray CT inspection apparatus is supported;

moving said first and second X-ray sources and detectors of said X-ray CT inspection apparatus synchronously in parallel along respective paths on either side of the freight container;

carrying out an inspection of the contents of the freight container according to said first X-ray beam from said tip end of the freight container to a substantially central portion of the freight container, and carrying out an inspection of the contents of the freight container according to said second X-ray beam from said substantially central portion of the freight container to a trailing end of the freight container while effecting relative displacement between the freight container and the X-ray CT inspection apparatus, and displaying a condition of an interior portion of the freight container while moving said X-ray CT inspection apparatus in synchronism with a starting of the X-ray CT inspection; and rotating said X-ray CT inspection apparatus through a predetermined angle while maintaining the freight container at the same stopped position, said X-ray CT inspection apparatus being rotatable around the freight container along a path having a portion extending within the pit.

13. X-ray CT inspection equipment inspecting the contents of for a freight container comprising:

a detector;

a X-ray source;

an annular-shaped rotatable table for mounting said detector and said X-ray source;

a movement unit;

a hollow-shaped vertical stand member provided vertically on said movement unit so as to be moved thereby horizontally, said annular-shaped rotatable table being provided on a side face of said hollow-shaped vertical stand member; and a freight container transportation rail for transporting the freight container extending horizontally through said hollow-shaped vertical stand member and a hollow portion of said annular-shaped rotatable table so that when the freight container transported on said freight container transportation rail is positioned at a hollow portion of said annular-shaped rotatable table, contents of an interior portion of the freight container are computerized-tomography-inspected by rotating said annular-shaped rotatable table.

14. X-ray CT inspection equipment for inspecting the contents of a freight container comprising:

a detector;

a X-ray source;

two annular-shaped rotatable tables each mounting a detector and a X-ray source;

a movement unit;

a hollow-shaped vertical stand member provided vertically on said movement unit so as to be moved thereby horizontally, said two annular-shaped rotatable tables being symmetrically disposed on respective side faces of said hollow-shaped vertical stand member; and a freight container transportation rail for transporting the freight container extending horizontally through said hollow-shaped vertical stand member and hollow portions of said two annular-shaped rotatable tables so that when the freight container transported on said freight container transportation rail is positioned at hollow portions of said two annular-shaped rotatable tables, contents of an interior portion of the freight container are computerized-tomography-inspected by rotating said two annular-shaped rotatable tables.

15. A method of inspecting the contents of a freight container using X-ray CT inspection, comprising the steps of:

transporting a freight container on a trolley into an inspection building through a freight container inlet port to an inspection position in the vicinity of a X-ray CT inspection apparatus having an X-ray source and a detector;

stopping said trolley when a tip end of the freight container reaches an inspection position of said X-ray CT inspection apparatus;

moving the X-ray source and detector of said X-ray CT inspection apparatus synchronously in parallel along respective paths on either side of the freight container while the freight container is stopped;

computerized-tomographing an interior portion of the freight container by irradiating a X-ray beam thereon from said X-ray source;

displaying a condition of an interior portion of contents accommodated in the freight container; and rotating said X-ray CT inspection apparatus through a predetermined angle while maintaining the freight container at the same stopped position.

16. A method according to claim 15, wherein the freight container is a non-portable freight container, the step of transporting the freight container on the trolley including transporting the freight container on the trolley arranged for movement along a freight container transportation rail.

17. A method of inspecting the contents of a freight container using X-ray CT inspection, comprising the steps of:

(a) mounting a freight container which is stored in a storage yard on a trolley;

(b) transporting said trolley on a transportation rail into an inspection building through a freight container inlet port to an inspection station in the vicinity of a X-ray CT inspection apparatus having an X-ray source and a detector mounted on a rotatable table;

(c) stopping said trolley when a tip end of the freight container reaches an inspection position of said X-ray CT inspection apparatus;

(d) moving the X-ray source and the detector of said X-ray CT inspection apparatus synchronously in parallel along respective paths on either side of the freight container while the freight container is stopped;

(e) computerized-tomographing an interior portion of the freight container by irradiating a X-ray beam thereon from said X-ray source;

(f) displaying a condition of an interior portion of contents accommodated in the freight container;

(g) rotating said table through a predetermined angle while maintaining said freight container at the same stopped position;

(h) repeating steps (d) through (g) until said table has rotated through 180°;

(i) moving said trolley in a predetermined distance along said rail to move the freight container an incremental amount at the inspection position; and (j) repeating steps (d) through (i) until the freight container has been completely inspected.

18. A method of inspecting the contents of a freight container using X-ray CT inspection, comprising the steps of:

setting a freight container at a predetermined position of a stand member having a freight container transportation rail;

aligning a tip end of the freight container with a X-ray beam irradiated from a X-ray source of a X-ray CT inspection apparatus having a detector for detecting the X-ray beam;

moving the X-ray source and the detector of said X-ray CT inspection apparatus synchronously in parallel along respective paths on either side of the freight container;

carrying out a CT inspection by computerized-tomography of an interior portion of the freight container by irradiating the X-ray beam from said X-ray source on the freight container, and displaying a condition of an interior portion of the freight container while moving said X-ray CT inspection apparatus to a finish end portion of the freight container in synchronism with a starting of the X-ray CT inspection; and rotating said X-ray CT inspection apparatus through a predetermined angle while maintaining the freight container at the same stopped position.

* * * * *